(12) United States Patent
Sakamoto et al.

(10) Patent No.: US 11,075,003 B2
(45) Date of Patent: Jul. 27, 2021

(54) ASSISTANCE APPARATUS FOR ASSISTING INTERPRETATION REPORT CREATION AND METHOD FOR CONTROLLING THE SAME

(71) Applicant: CANON KABUSHIKI KAISHA, Tokyo (JP)

(72) Inventors: Ryo Sakamoto, Kyoto (JP); Masami Kawagishi, Kawasaki (JP); Gakuto Aoyama, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 418 days.

(21) Appl. No.: 15/503,804

(22) PCT Filed: Aug. 31, 2015

(86) PCT No.: PCT/JP2015/004398
§ 371 (c)(1),
(2) Date: Feb. 14, 2017

(87) PCT Pub. No.: WO2016/035312
PCT Pub. Date: Mar. 10, 2016

(65) Prior Publication Data
US 2017/0243348 A1      Aug. 24, 2017

(30) Foreign Application Priority Data
Sep. 5, 2014   (JP) .............................. JP2014-181591

(51) Int. Cl.
*G06K 9/00*      (2006.01)
*G16H 30/20*     (2018.01)
(Continued)

(52) U.S. Cl.
CPC ............. *G16H 30/20* (2018.01); *A61B 5/748* (2013.01); *A61B 6/032* (2013.01); *A61B 6/465* (2013.01);
(Continued)

(58) Field of Classification Search
CPC .. G06K 9/00; G06K 9/00335; G06K 9/00442; G06K 9/00597; G06K 9/03;
(Continued)

(56) References Cited

U.S. PATENT DOCUMENTS 8,423,571 B2 *   4/2013   Moriya ................. G16H 15/00
                                                          707/769
9,361,580 B2     6/2016   Kawagishi ............... G06N 5/02
(Continued)

FOREIGN PATENT DOCUMENTS

JP   2006-059063    3/2006
JP   2006-271528   10/2006
(Continued)

OTHER PUBLICATIONS

Kamiyama et al., "Simultaneous segmentation of multi-organ from an abdominal CT volume using fusion move graph cuts", IEICE Technical Report, MI2010-122 and 2011-01 (2011) 217-22.

*Primary Examiner* — Eric Rush
(74) *Attorney, Agent, or Firm* — Venable LLP

(57) ABSTRACT

An assistance apparatus for assisting creation of an interpretation report obtains a set of regions of interest, which are determined as regions that were observed, of medical image data of a subject that is displayed as an interpretation target, and a set of described regions, which are regions that correspond to description of an interpretation report about the medical image data of a subject. The assistance apparatus determines consistency between the set of regions of
(Continued)

interest and the set of described regions, and lets a display unit display a result of the determination.

12 Claims, 9 Drawing Sheets

(51) Int. Cl.
| | |
|---|---|
| *A61B 6/03* | (2006.01) |
| *G06F 3/01* | (2006.01) |
| *G06F 3/0488* | (2013.01) |
| *A61B 5/00* | (2006.01) |
| *G06Q 10/10* | (2012.01) |
| *A61B 6/00* | (2006.01) |
| *A61B 8/00* | (2006.01) |
| *G16H 30/40* | (2018.01) |
| *G16H 15/00* | (2018.01) |
| *G16H 50/20* | (2018.01) |
| *G06K 9/03* | (2006.01) |
| *G06T 7/11* | (2017.01) |
| *A61B 8/13* | (2006.01) |
| *G06T 7/00* | (2017.01) |
| *A61B 5/055* | (2006.01) |
| *A61B 8/14* | (2006.01) |

(52) U.S. Cl.
CPC ............ *A61B 6/467* (2013.01); *A61B 6/468* (2013.01); *A61B 6/469* (2013.01); *A61B 8/13* (2013.01); *A61B 8/465* (2013.01); *A61B 8/468* (2013.01); *A61B 8/469* (2013.01); *G06F 3/013* (2013.01); *G06F 3/0488* (2013.01); *G06K 9/03* (2013.01); *G06Q 10/10* (2013.01); *G06T 7/0012* (2013.01); *G06T 7/11* (2017.01); *G16H 15/00* (2018.01); *G16H 30/40* (2018.01); *G16H 50/20* (2018.01); *A61B 5/055* (2013.01); *A61B 5/7435* (2013.01); *A61B 8/00* (2013.01); *A61B 8/14* (2013.01)

(58) Field of Classification Search
CPC ............ G06K 9/033; G06K 9/34; G06K 9/36; G06K 9/6262; G06K 9/6263; G06K 9/6264; G06K 9/6265; G06K 2209/05; G06K 2209/051; G06K 2209/053; G06K 2209/055; G06T 7/0012; G06T 7/0014; G06T 7/0016; G06T 7/10; G06T 7/11; G06T 2207/30004; G06T 2207/30008; G06T 2207/30016; G06T 2207/30061; G06T 2207/30064; G06T 2207/30068; G06T 2207/30096; G06Q 50/22; G06Q 50/24; G16H 10/40; G16H 10/60; G16H 15/00; G16H 30/00; G16H 30/20; G16H 30/40; G16H 50/00; G16H 50/20; G06F 3/013; G06F 3/0488; G06F 19/30; G06F 19/34; A61B 5/05; A61B 5/055; A61B 5/743; A61B 5/7435; A61B 5/748; A61B 5/7485; A61B 6/032; A61B 6/46; A61B 6/461; A61B 6/463; A61B 6/465; A61B 6/467; A61B 6/468; A61B 6/469; A61B 6/52; A61B 6/5205; A61B 6/5211; A61B 6/5217; A61B 6/5294; A61B 8/00; A61B 8/13; A61B 8/14; A61B 8/461; A61B 8/463; A61B 8/465; A61B 8/467; A61B 8/468; A61B 8/469; A61B 8/52; A61B 8/5207; A61B 8/5215; A61B 8/5223; A61B 8/5292
USPC ....... 382/100, 103, 128, 132, 224, 229, 278, 382/282, 291, 292, 305, 309, 311; 600/300; 128/920, 922–924; 705/2, 3, 705/7.11, 7.38, 7.41, 7.42; 345/157, 173
See application file for complete search history.

(56) References Cited

U.S. PATENT DOCUMENTS

| | | | |
|---|---|---|---|
| 9,519,866 B2 | 12/2016 | Kawagishi et al. | ... G06N 7/005 |
| 9,841,811 B2 * | 12/2017 | Reiner | ................ A61B 6/465 |
| 2007/0219651 A1 * | 9/2007 | Kawakami | .............. G06F 3/038 |
| | | | 345/635 |
| 2008/0062383 A1 * | 3/2008 | Endrikhovski | ......... G06F 3/013 |
| | | | 351/209 |
| 2009/0089091 A1 * | 4/2009 | Sawasaki | ............... G06F 19/321 |
| | | | 705/2 |
| 2010/0256459 A1 * | 10/2010 | Miyasa | .................. G06Q 50/22 |
| | | | 600/300 |
| 2011/0002515 A1 * | 1/2011 | Futami | .................. G06F 19/321 |
| | | | 382/128 |
| 2011/0066635 A1 * | 3/2011 | Moriya | .................. G16H 15/00 |
| | | | 707/769 |
| 2011/0199390 A1 | 8/2011 | Iizuka et al. | ................... 345/629 |
| 2011/0206283 A1 * | 8/2011 | Quarfordt | ............ G06K 9/0061 |
| | | | 382/220 |
| 2011/0213748 A1 | 9/2011 | Kawagishi et al. | ............ 706/52 |
| 2012/0254101 A1 | 10/2012 | Kawagishi | ....................... 706/52 |
| 2013/0051646 A1 | 2/2013 | Nakano et al. | ................ 382/131 |
| 2014/0195472 A1 | 7/2014 | Kawagishi | ............... G06N 5/06 |
| 2014/0379364 A1 * | 12/2014 | Liu | ........................ G16H 15/00 |
| | | | 705/2 |
| 2015/0146947 A1 * | 5/2015 | Matsumoto | .......... G06K 9/6253 |
| | | | 382/128 |
| 2015/0262014 A1 * | 9/2015 | Iwamura | ................ G06K 9/6253 |
| | | | 382/128 |
| 2015/0279061 A1 * | 10/2015 | Kutsuna | ................ G06T 7/0012 |
| | | | 382/131 |
| 2016/0292392 A1 * | 10/2016 | Xu | ......................... G06F 16/353 |
| 2016/0335394 A1 | 11/2016 | Kawagishi et al. | .. G06F 19/321 |
| 2016/0335764 A1 | 11/2016 | Kawagishi et al. | .. G06T 7/0012 |

FOREIGN PATENT DOCUMENTS

| | | |
|---|---|---|
| JP | 2007-319327 | 12/2007 |
| JP | 2009-045131 | 3/2009 |

* cited by examiner

[Fig. 1]
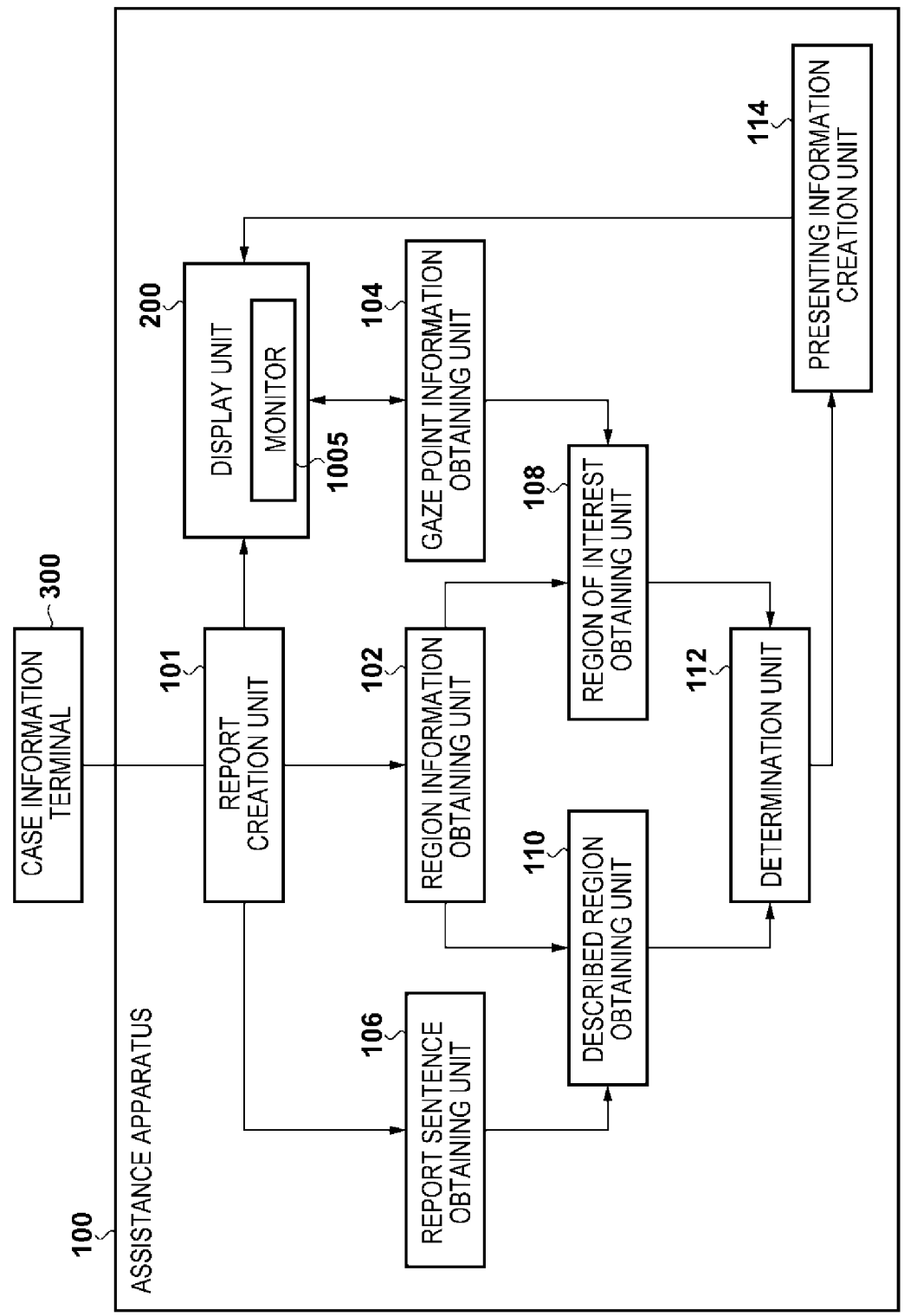

[Fig. 2]
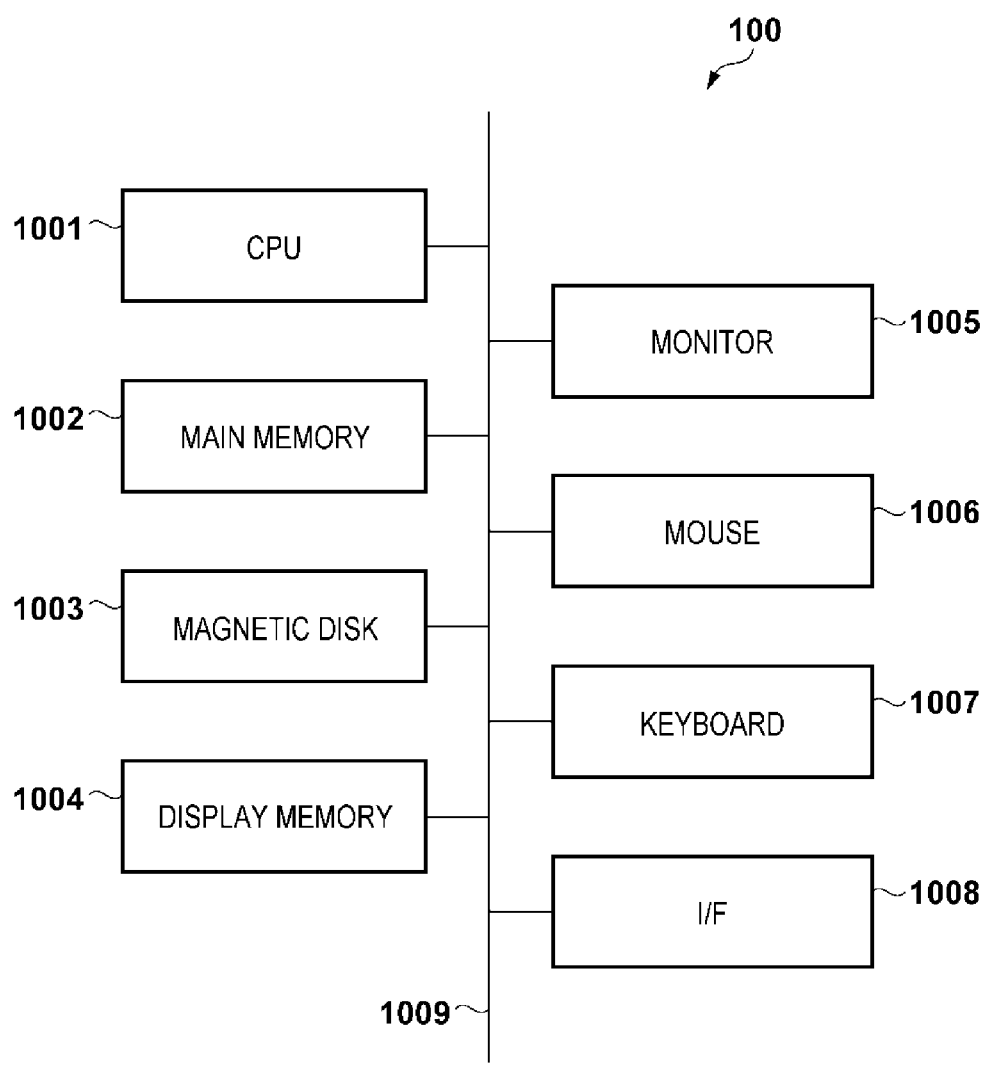

[Fig. 3]
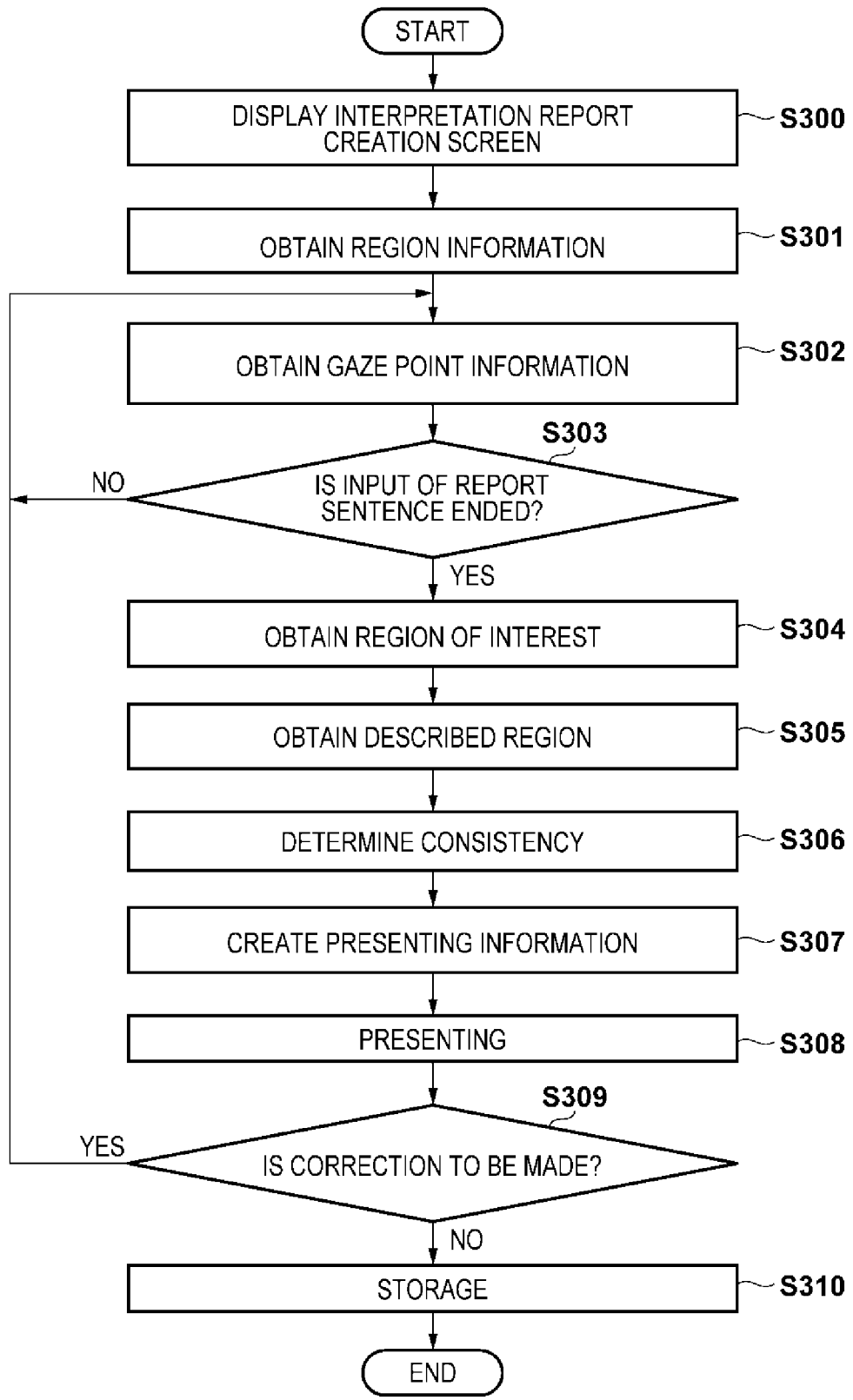

[Fig. 4A]

| (x, y, z) | LABEL |
|---|---|
| (0, 0, 0) | 0 : OUTSIDE BODY SURFACE |
| (0, 0, 1) | 0 : OUTSIDE BODY SURFACE |
| . . . | |
| $(x_{rul}, y_{rul}, z_{rul})$ | 1 : RIGHT UPPER LOBE |
| . . . | |
| $(x_1, y_1, z_1)$ | 7 : LIVER |
| . . . | |

[Fig. 4B]

1 : RIGHT UPPER LOBE $[\{(x > x_{rull}) \wedge (x < x_{rulr})\} \wedge \{y > y_{rulu}) \wedge (y < y_{ruld})\} \wedge \{z > x_{rult}) \wedge (x < x_{rulb})\}] \vee$

. . .

7 : LIVER $[\{(x > x_{ll}) \wedge (x < x_{lr})\} \wedge \{y > y_{lu}) \wedge (y < y_{ld})\} \wedge \{z > x_{lt}) \wedge (x < x_{lb})\}] \vee$

. . .

[Fig. 5]
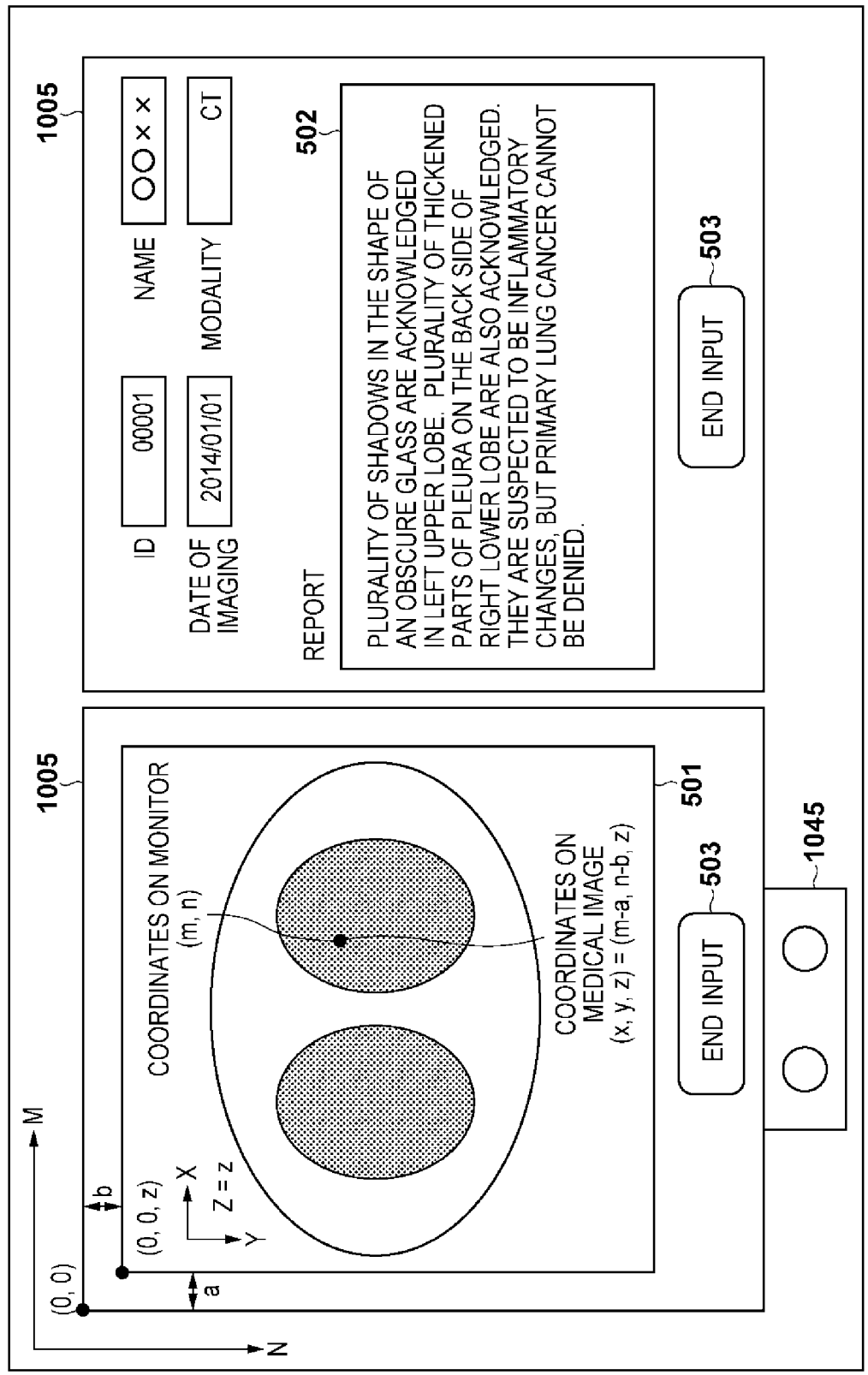

[Fig. 6]

| LABEL | |
|---|---|
| ... | |
| 0 : OUTSIDE BODY SURFACE | |
| ... | |
| 9 : OTHERS | |
| ... | |
| 2 : RIGHT INTERMEDIATE LOBE | |
| 1 : RIGHT UPPER LOBE | |
| ... | |
| 4 : LEFT UPPER LOBE | |
| 5 : LEFT LOWER LOBE | |
| ... | |
| 3 : RIGHT LOWER LOBE | |
| ... | |

REGION INFORMATION

| | (x, y, z) |
|---|---|
| $O_t$ | (4, 4, 6) |
| $O_1$ | (4, 5, 6) |
| $O_2$ | |
| $O_3$ | (5, 4, 6) |
| ... | |

GAZE POINT INFORMATION

[Fig. 7]
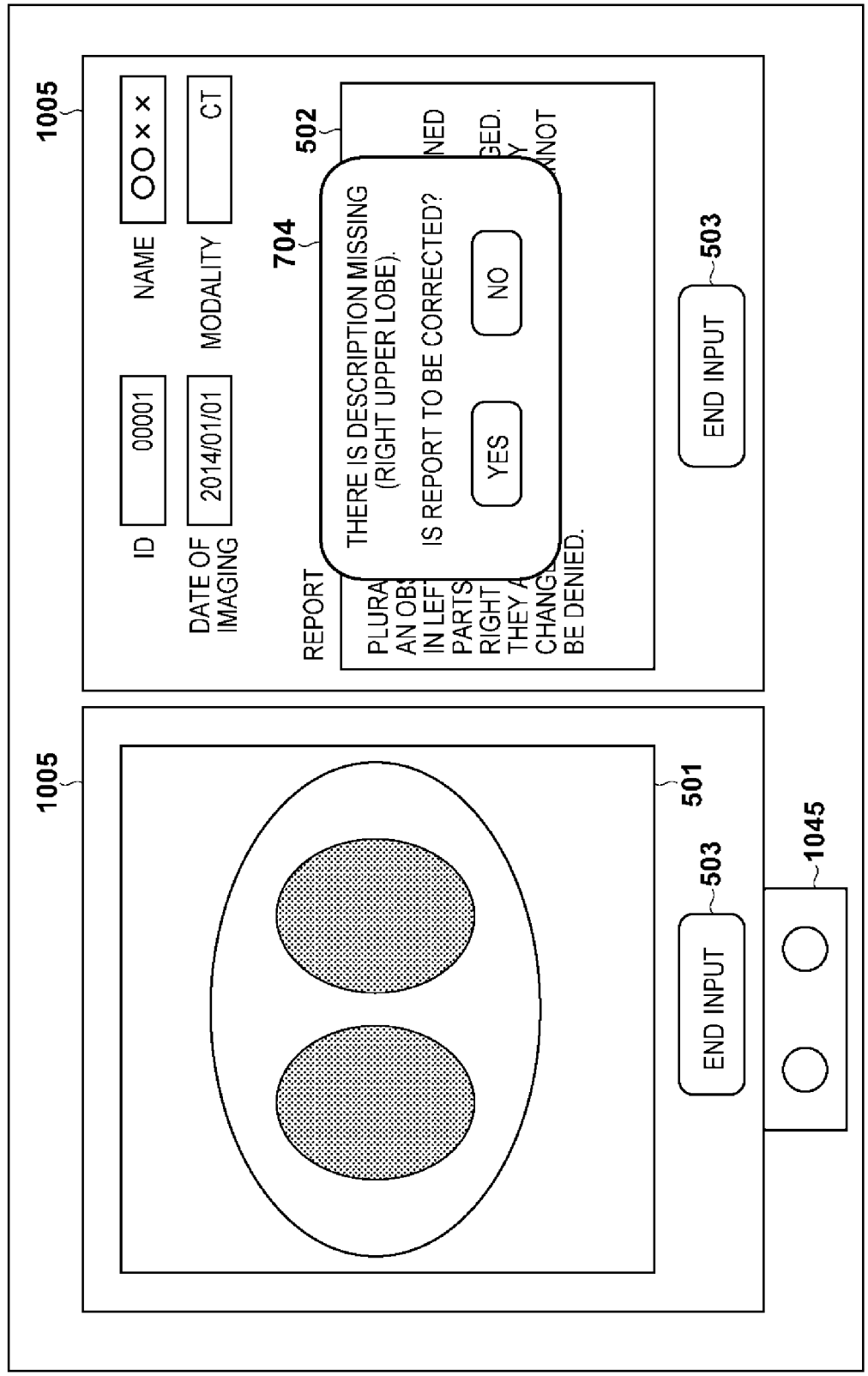

[Fig. 8]
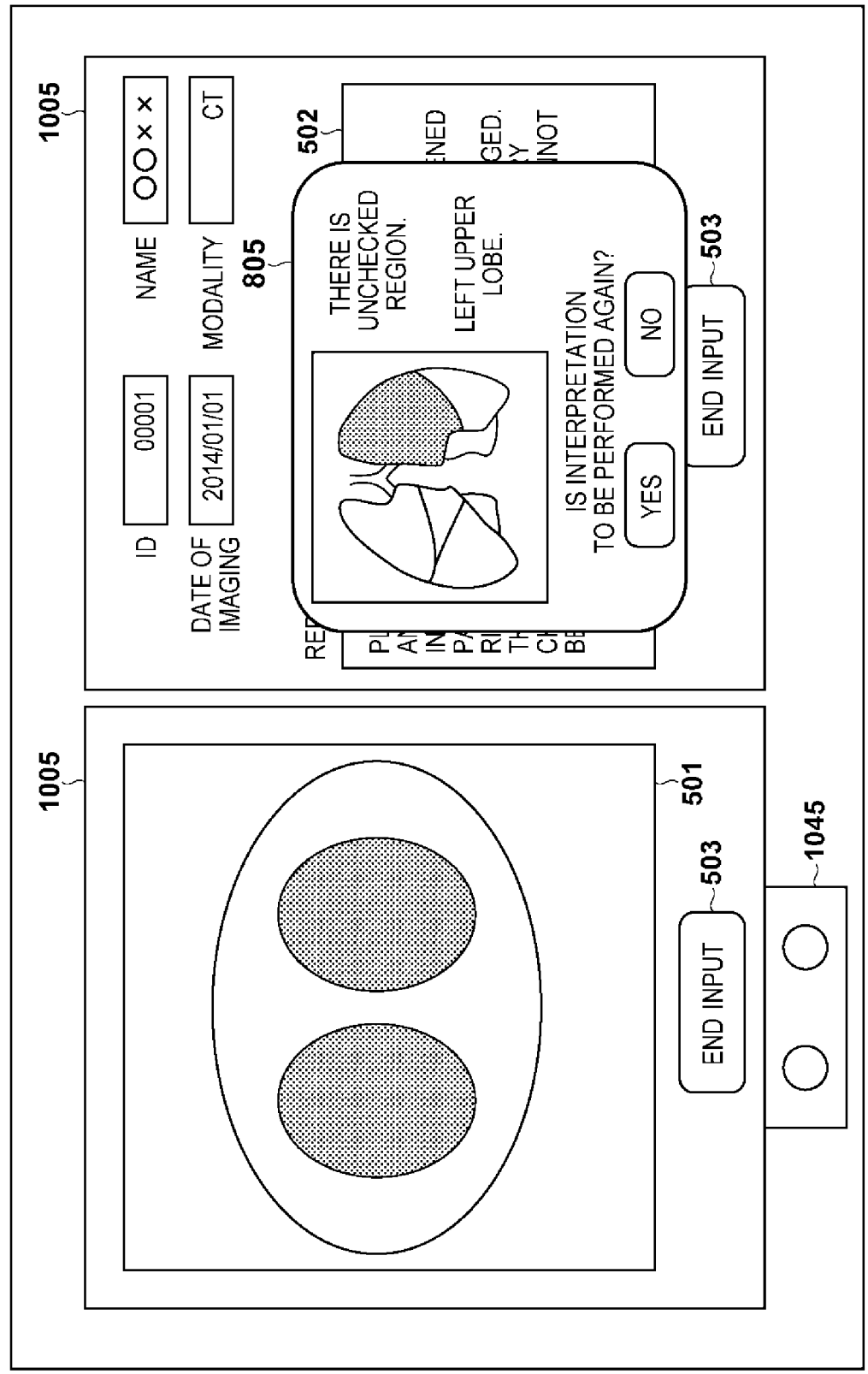

[Fig. 9A]
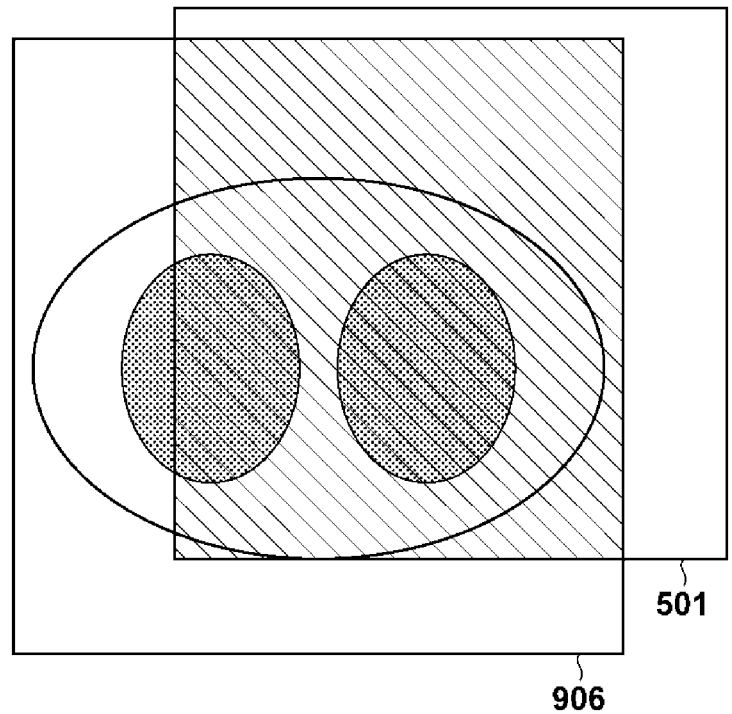
[Fig. 9B]
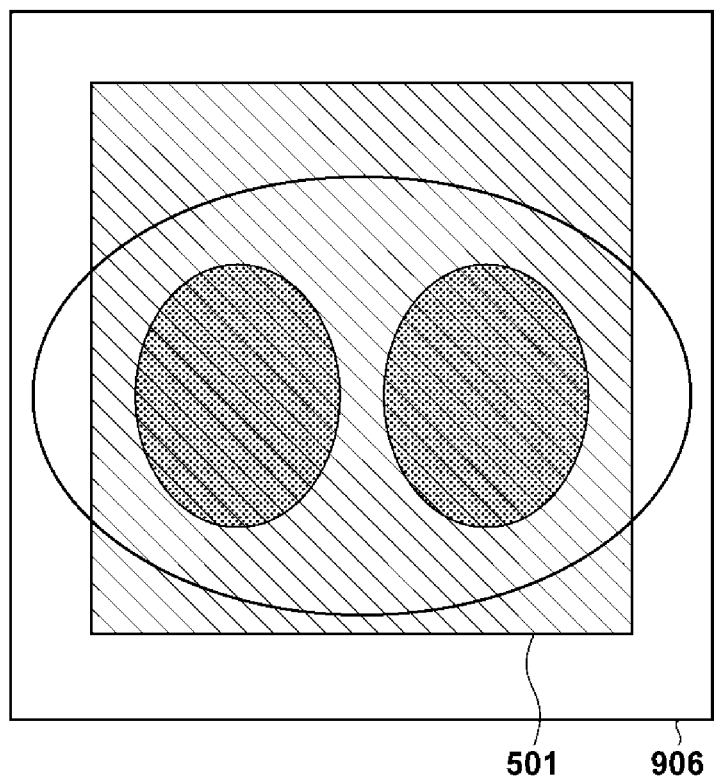

ASSISTANCE APPARATUS FOR ASSISTING INTERPRETATION REPORT CREATION AND METHOD FOR CONTROLLING THE SAME

TECHNICAL FIELD

The present invention relates to an assistance apparatus for assisting creation of an interpretation report, and a method for controlling the same.

BACKGROUND ART

In the medical field, image diagnosis is performed in which a medical doctor interprets medical image data obtained by an imaging apparatus, such as an X-ray computed tomography apparatus or an MRI, so as to perform diagnosis. In the image diagnosis, in response to an interpretation request from an attending doctor, a medical doctor comprehensively judges a remark (interpretation remark) obtained from an image and various types of measured values, and specifies a symptom of a pathological abnormality in the image. Then, the medical doctor creates, for the attending doctor who made the request, an interpretation report showing why this diagnosis was made using the interpretation remark and the measured values.

In the creation of such an interpretation report, a technique is known for detecting a gaze point of the interpreter and recognizing the state of checking of the medical image data at the time of creating the interpretation report. Japanese Patent Laid-Open No. 2009-045131 (hereinafter, Patent Document 1) discloses a technique for storing input information at the time of creating a report and an observed portion of the medical image data (interest information) at the time of inputting that input information in association with each other. According to this technique, it is possible to recognize a portion of the medical image data in which a medical doctor was interested when the interpretation report was created. Japanese Patent Laid-Open No. 2006-271528 (hereinafter, Patent Document 2) discloses a technique in which an observation area to be observed is specified using examination information and a computer-assisted diagnosis function, and it is determined based on gaze point information indicating whether or not the specified observation area has been checked. According to this technique, it is possible to recognize whether or not a predetermined area to be observed has been checked.

However, in Patent Document 1, the input information and the interest information are merely stored in association with each other, without taking into consideration a region of interest that is not input (region in which a user was interested but that is not described in the report) and the consistency between the input information and the interest information. Furthermore, according to the technique of Patent Document 2, it is possible to determine whether or not input was made regarding a predetermined observation area that is to be observed, but it is impossible to determine whether or not input was made regarding a region that is not predetermined. In other words, when a medical doctor has remarked on a region that he or she was not prompted to observe but has forgotten to input this region (hereinafter, referred to as missing description), it is impossible to call attention. Furthermore, since the consistency between the input content and the interest information is not considered, it is impossible to call attention to an inconsistency (hereinafter, referred to as a checking failure) such that, for example, a region designated in an input content is not present in the interest information.

SUMMARY OF INVENTION

According to an embodiment of the present invention, provided is an assistance apparatus for assisting in creation of an appropriate interpretation report while reducing occurrence of missing description and/or a checking failure, and a method for controlling the same.

According to one aspect of the present invention, there is provided an assistance apparatus for assisting creation of an interpretation report comprising: first obtaining means for obtaining a set of regions of interest, which are determined as regions that were observed, of medical image data of a subject that is displayed as an interpretation target; second obtaining means for obtaining a set of described regions, which are regions that correspond to description of an interpretation report about the medical image data; determination means for determining consistency between the set of regions of interest and the set of described regions; and display control means for controlling a display unit to display a result of the determination by the determination means.

According to another aspect of the present invention, there is provided a method for controlling an assistance apparatus for assisting creation of an interpretation report, comprising: a first obtaining step of obtaining a set of regions of interest, which are determined as regions that were observed, of medical image data of a subject that is displayed as an interpretation target; a second obtaining step of obtaining a set of described regions, which are regions that correspond to description of an interpretation report about the medical image data of the subject; a determination step of determining consistency between the set of regions of interest and the set of described regions; and a display control step of controlling a display unit to display a result of the determination in the determination step.

According to another aspect of the present invention, there is provided an apparatus for assisting medical diagnosis, the apparatus comprising: at least one processor; a memory storing a program including instructions executed by the processor to perform a process including: obtaining a set of regions of interest, which are determined as regions that were observed, of medical image data of a subject that is displayed as an interpretation target; obtaining a set of described regions, which are regions that correspond to description of an interpretation report about the medical image data of the subject; determining consistency between the set of regions of interest and the set of described regions; and controlling a display unit to display a result in the determining.

Further features of the present invention will become apparent from the following description of exemplary embodiments with reference to the attached drawings.

BRIEF DESCRIPTION OF DRAWINGS

FIG. 1 is a block diagram illustrating an example of a functional configuration of an interpretation report creation assistance apparatus.

FIG. 2 is a block diagram illustrating an example of a hardware configuration of the interpretation report creation assistance apparatus.

FIG. 3 is a flowchart illustrating the procedure of interpretation report creation assistance processing according to the embodiment.

FIG. 4A is a diagram illustrating an example of a data configuration of region information.

FIG. 4B is a diagram illustrating an example of a data configuration of region information.

FIG. 5 is a diagram illustrating an example of display on a monitor at the time of interpretation.

FIG. 6 is a diagram illustrating extraction of a gaze region.

FIG. 7 is a diagram illustrating an example of display of presenting information according to a first embodiment.

FIG. 8 is a diagram illustrating an example of display of presenting information according to a second embodiment.

FIG. 9A is a diagram illustrating another example of a region of interest.

FIG. 9B is a diagram illustrating another example of a region of interest.

DESCRIPTION OF EMBODIMENTS

Hereinafter, preferred embodiments of the present invention will be described with reference to the accompanying drawings. Note that the scope of the invention is not limited to the exemplified drawings.

First Embodiment

An interpretation report creation assistance apparatus according to a first embodiment obtains medical information (such as medical image data or information on an electronic medical chart) concerning a case that serves as a diagnosis target, and input information (such as user's gaze point information or a report sentence) input by a user, so as to assist in creation of an interpretation report concerning the case. The "user" refers to, for example, an interpreter who interprets medical image data. The following will describe a case where three-dimensional chest X-ray CT image data is used as an example of medical image data. The target of assistance in interpretation according to the present invention is, of course, not limited to this, and the present invention is applicable to, for example, assistance in interpretation of a two-dimensional image taken by simple X-ray imaging, an ultrasound tomography image, and the like. Every embodiment below is merely an example for illustrating the procedure of processing of the interpretation report creation assistance apparatus.

FIG. 1 shows an example of a functional configuration of an interpretation report creation assistance apparatus (hereinafter, an assistance apparatus 100) according to a first embodiment. The assistance apparatus 100 according to the first embodiment is connected to a display unit 200 and a case information terminal 300. The display unit 200 has a monitor 1005 (FIG. 2), and displays various types of information in accordance with instructions of a system or a user. Specific contents that are displayed on the monitor 1005 will be described later.

The case information terminal 300 obtains, from a server (not shown), medical information relating to a case that serves as a diagnosis target, for example, medical information on a lung abnormal shadow (such as three-dimensional medical image data or electronic medical chart information). Alternatively, the case information terminal 300 may be connected to an external storage device such as FDD, HDD, CD drive, a DVD drive, a MO drive, or a ZIP drive, and may obtain the medical information from the drive. Furthermore, the case information terminal 300 obtains additional data (clinical data such as a tumor marker value, a report on past cases of a target patient, and the like) on the lung abnormal shadow, in accordance with a request from the user. The obtained medical information and additional data are transmitted to the assistance apparatus 100 via a LAN or the like.

The assistance apparatus 100 is provided with a report creation unit 101, a region information obtaining unit 102, a gaze point information obtaining unit 104, a report sentence obtaining unit 106, a region of interest obtaining unit 108, a described region obtaining unit 110, a determination unit 112, and a presenting information creation unit 114. Note that the assistance apparatus 100 and the case information terminal 300 are shown as separate apparatuses, but may be formed into one piece.

The report creation unit 101 performs overall processing at the time of creating a report. For example, the report creation unit 101 displays an interpretation report creation screen (described later with reference to FIG. 5) on the monitor 1005 of the display unit 200. The interpretation report creation screen displays the medical information (medical image data) serving as an interpretation target that is received from the case information terminal 300, and the user interprets the displayed medical image data and inputs an interpretation report using a keyboard 1007 and the like, which will be described later. Accordingly, the user can perform interpretation by observing the displayed medical information (such as medical image data).

The region information obtaining unit 102 obtains association information (region information) in which coordinate positions of the medical image data transmitted from the case information terminal 300 are associated with regions. More specifically, the region information obtaining unit 102 obtains association information in which coordinate positions of the medical image data are associated with medically divided regions. In the present embodiment, the medically divided regions may be anatomical structures (for example, heart, liver, right upper lobe, and the like). The region information obtaining unit 102 outputs the obtained association information to the region of interest obtaining unit 108 and the described region obtaining unit 110. Note that obtainment of such region information can be realized by subjecting the medical image data to a well-known segmentation method and associating segmentation results with coordinate positions of an image. Examples of such a segmentation method include a technique for simultaneously extracting a plurality of abdominal organs: "Simultaneous segmentation of multi-organ from an abdominal CT volume using fusion move graph cuts", Kamiyama et al., (IEICE technical report, MI2010-122 and 2011-01). Note that the region information may be obtained by the region information obtaining unit 102 analyzing the medical image data serving as an interpretation target, or may be included in advance in the medical image data transmitted from the case information terminal 300. Alternatively, a user may manually designate a region and a name that correspond to an anatomical structure.

The gaze point information obtaining unit 104 obtains gaze point information, which indicates a position on medical image data that a user gazed at. In the present embodiment, the gaze point information obtaining unit 104 detects a gaze point on the monitor 1005, and obtains a coordinate position of the corresponding medical image data based on the displayed position of the medical image data on the monitor 1005 and the coordinates of the detected gaze point, the obtained coordinate position serving as the gaze point information. The obtained gaze point information is output to the region of interest obtaining unit 108. Note that the gaze point information obtaining unit 104 may realize the detection of a gaze point on the monitor using, for example, a gaze point tracking device 1045 (FIG. 5) such as a video camera or an eye tracker that is capable of simultaneous imaging from multiple observing points. Specifically, the face and eyes of the user are shot from a plurality of observing points, and a stereo image obtained by the shooting is subjected to predetermined image recognition processing, thereby making it possible to detect a coordinate position of a place on the monitor to which a gaze point is attracted. The gaze point tracking device 1045 is disposed, for example, at an end of the monitor (for example, immediately below the monitor).

A report sentence obtaining unit 106 obtains a report sentence (text data) that was input using the interpretation report creation screen, the report sentence being a result of interpretation of the medical image data by the user. The obtained report sentence is output to the described region obtaining unit 110.

The region of interest obtaining unit 108 obtains, from among medically divided regions (for example, regions divided based on the anatomical structure) of the displayed medical image data, a set of regions of interest, which are regions that the user observed at the time of interpretation. For example, the region of interest obtaining unit 108 obtains the regions of interest, which are regions that the user observed, of the displayed medical image data based on the region information obtained by the region information obtaining unit 102 and the gaze point information obtained by the gaze point information obtaining unit 104. Specific contents of the regions of interest will be described later. The obtained regions of interest are output to the determination unit 112.

The described region obtaining unit 110 obtains a set of described regions, which are medical regions (for example, regions based on the anatomical structure) described in the report sentence for the medical image data. For example, the described region obtaining unit 110 obtains described regions based on the region information obtained by the region information obtaining unit 102 and the report sentence obtained by the report sentence obtaining unit 106. The obtained described regions are output to the determination unit 112.

Based on the set of regions of interest obtained by the region of interest obtaining unit 108 and the set of described regions obtained by the described region obtaining unit 110, the determination unit 112 determines the consistency between the regions of interest and the described regions. The determined result is output to the presenting information creation unit 114. The presenting information creation unit 114 creates presenting information based on the determination result of the determination unit 112. The created presenting information is output to, for example, the display unit 200, and is presented on the monitor 1005.

Note that at least some of the constituent components of the assistance apparatus 100 shown in FIG. 1 may be realized as independent devices. Furthermore, the constituent components may respectively be realized as software that realizes the functions. According to the present embodiment, it is assumed that the respective constituent components are realized by a computer executing predetermined pieces of software.

FIG. 2 is a diagram showing a basic hardware configuration of a computer device for realizing the functions of the respective constituent components shown in FIG. 1 by executing the pieces of software. That is, the assistance apparatus 100 according to the present embodiment can be realized by the computer device. The CPU 1001 mainly controls operations of the respective constituent components. A main memory 1002 stores a control program that is executed by the CPU 1001, and provides a work area for use when the program is executed by the CPU 1001. A magnetic disk 1003 stores, for example, various types of application software including an operating system (OS), a device drive for driving a peripheral device, and a program for performing processing that will be described later and the like.

A display memory 1004 temporarily stores data to be displayed. The monitor 1005 is, for example, a CRT monitor, a liquid crystal monitor, or the like, and displays an image or text based on data from the display memory 1004. A mouse 1006 and the keyboard 1007 respectively perform pointing input and input of characters and the like by a user. An interface 1008 connects the assistance apparatus 100 to a network or the like. For example, the case information terminal 300 is connected to the assistance apparatus 100 via the interface 1008. The above-described constituent components are communicably connected to each other via a common bus 1009.

Hereinafter, processing (processing for assisting in report creation at the time of interpretation) performed by the assistance apparatus 100 having the above-described configuration according to the present embodiment will be described with reference to the flowchart of FIG. 3. In the present embodiment, the processing is realized by the CPU 1001 executing programs for realizing the functions of the constituent components, the programs being stored in the main memory 1002. Note that in the following description, positions (pixels) on the screen of the monitor 1005 are indicated by the MN coordinate system, and positions (voxels) in medical image data are indicated by the XYZ coordinate system. Furthermore, in the following description, the gaze point information obtaining unit 104 performs detection at a predetermined sampling rate (for example, 0.1 second) so as to obtain gaze point information. The gaze point information at an arbitrary point of time is indicated as "Ot (otx, oty, otz)" (t=1, 2 . . . ).

In step S300, the report creation unit 101 displays an interpretation report creation screen on the monitor 1005. As shown in FIG. 5, the interpretation report creation screen includes a tomographic image display region 501 in which medical image data serving as an interpretation target is displayed, a report sentence input region 502 that accepts an input of a report (text data) by a user, and interpretation end buttons 503. For example, an axial tomographic image of medical image data is displayed in the tomographic image display region 501. Note that two screens shown in FIG. 5 may be displayed simultaneously on a single monitor screen, may be displayed in a switched manner on a single monitor screen, or may be displayed separately on two monitors. According to the present embodiment, the two screens are displayed separately on two monitors, and the operation for obtaining gaze point information, which will be described later, is performed on the monitor on which medical image data is displayed.

Then, in step S301, the region information obtaining unit 102 obtains the medical image data transmitted from the case information terminal 300, that is, an association information (region information) in which coordinate positions of the medical image data serving as an interpretation target are associated with anatomical structures of a subject. This region information is obtained as a correspondence table in which, for example, different labels are assigned to the anatomical structures and each voxel is associated with any of the labels. Alternatively, the region information may be in a form of conditional equations. The respective examples are shown in FIGS. 4A and 4B. FIG. 4A shows region information in which each voxel is associated with a label indicating an anatomical structure. Furthermore, FIG. 4B shows region information in which a voxel coordinate range is defined for each anatomical structure label. The region information may, of course, be configured in another form. The following will describe the case where region information in the form of a correspondence table as shown in FIG. 4A is obtained.

Then, in step S302, the gaze point information obtaining unit 104 obtains gaze point information indicating a position of the medical image data that the user gazed at. Furthermore, during this step, the report sentence obtaining unit 106 obtains a report sentence that is obtained by the user interpreting the medical image data and describing the interpretation result. In the present embodiment, the user can input, under control of the report creation unit 101, the report sentence in the report sentence input region 502 shown in FIG. 5 using the keyboard 1007.

Hereinafter, the obtainment of gaze point information by the gaze point information obtaining unit 104 will be described. FIG. 5 is an example in which an interpretation report creation screen and medical image data serving as the interpretation target are displayed on the monitors 1005. In this example, an axial tomographic image configured based on the medical image data is displayed. The axial tomographic image is a tomographic image that is perpendicular to the vertical direction of the body (cephalocaudal axis or body axis), and is indicated as a tomographic image on the XY plane at an arbitrary Z coordinate (an arbitrary position on the body axis) in the coordinate system of the present embodiment. The gaze point tracking device 1045 is provided below the monitor 1005, and detects the position (display pixel) on the monitor 1005 that the user is gazing at, as coordinates of the MN coordinate system.

Now, for ease of description, a case is considered in which the sizes of display pixels of the monitor and pixels of an axial tomographic image (on the XY plane) completely match each other. Furthermore, the correspondence relationship between coordinates (m, n) indicating the display pixels of the monitor and coordinates (x, y) of the pixels of an axial tomographic image is given as "x=m−a" and "y=n−b". In other words, a case is considered in which one voxel value of the medical image data is displayed by one pixel of the monitor. By giving an eye to one point (m, n) on the monitor in this state, x (=m−a) and y (=n−b) of the medical image data are determined. Furthermore, the positon of z is determined depending on the displayed axial tomographic image, and thus when the coordinates (m, n) on the monitor are determined, the coordinates (x, y, z) on the medical image data are uniquely determined. By utilizing this fact, it is possible to obtain the coordinates (that is, gaze point information) of a position on the medical image data to which a gaze point is attracted, based on the coordinates of gaze points on the monitor 1005 that is detected by the gaze point tracking device 1045.

Note that if the sizes of display pixels of the monitor and pixels of an axial tomographic image (on the XY plane) do not match each other, a ratio of the sizes of the pixels may be used to calculate the coordinates of positions on the medical image data. Furthermore, taking into consideration a field of view, coordinate positions on the medical image data that are indicated by surrounding pixels of the pixels of the axial tomographic image that correspond to the display pixels of the monitor 1005 may also be obtained as coordinates of positions to which gaze points are attracted. That is, a plurality of coordinate positions on the medical image data may also be obtained with respect to one gaze point that was obtained.

By pressing down the interpretation end button 503, the user notifies the assistance apparatus 100 of an end of input of the report sentence. Upon notification of the end of input of the report sentence, the procedure advances to step S303 from step S302. Note that if it is determined in step S303 that the interpretation end button 503 has not been pressed down, the procedure returns to step S302, and the processing for obtaining gaze point information and inputting a report sentence is continued.

In step S304, the region of interest obtaining unit 108 obtains a set of regions of interest based on the gaze points detected at the time of interpretation. That is, the region of interest obtaining unit 108 obtains, from among the medically divided regions of the medical image data, the regions of interest, which are regions that a user observed, based on the region information obtained in step S300 and the gaze point information obtained in step S301. An example of the method for determining whether or not a region A is a region of interest is a method in which:

(1) A number NoA of pixels (or voxels) in the region A shown in the tomographic image display region 501 in which a gaze point is detected at the time of interpretation is obtained;

(2) A total number of pixels (total number of voxels) NaA of the displayed region A is obtained, and if the ratio (NoA/NaA) of the number of the pixels in which a gaze point is detected to the total number of pixels included in the region A exceeds a predetermined value, it will be determined that the region A is a region of interest. Note that a method is also conceivable in which a region in which a time during which a gaze point was present in the region exceeds a predetermined time is determined as a region of interest, but the determination based only on the time results in the situation that the region A is determined as a region of interest although the entire region A is not viewed. Accordingly, a combination of the determination using a time during which a gaze point was present and the determination using the above-described ratio (NoA/NaA) is preferable. For example, it is preferable that the region A be determined as a region of interest when the ratio NoA/NaA exceeds a predetermined value and the total time in which a gaze point was present in the region A exceeds a predetermined time.

In the present embodiment, the procedures as described in the items (1) and (2) are used. More specifically, when a voxel in which a gaze point has at least once been detected is deemed as an observed region, and the number of the observed voxels is counted for each of the labels to which the anatomical structures are assigned. Then, based on the number of observed voxels for each label and the total number of voxels having this label, it is determined whether or not a medical doctor gazed at this label (that is, the corresponding anatomical structure). For example, when voxels whose ratio to the total number of voxels having an arbitrary label is larger than a predetermined ratio are observed, it is determined that the medical doctor gazed at the anatomical structure corresponding to this label, and the region of the anatomical structure is determined as a region of interest. Note that in the present specification, the region determined by the procedures of (1) and (2) is referred to as a gaze region. By determining the above-described gaze region as a region of interest, it is possible to determine the region of interest reflected by the observation state of the interpreter.

Description is given with reference to FIG. 6. In FIG. 6, the reference numeral 601 denotes an axial tomographic image at a Z position (Z=6) based on region information and gaze point information. The reference numeral 602 denotes the region information with respect to the axial tomographic image 601 that was obtained by the region information obtaining unit 102. Furthermore, the reference numeral 603 denotes the gaze point information obtained by the gaze point information obtaining unit 104.

The numeral given for each pixel (x, y) of the axial tomographic image 601 indicates the label that is shown in the region information 602 and is assigned to the corresponding voxel (x, y, 6). For example, the pixel (3, 7) (that is, the voxel (3, 7, 6)) has the label "1", showing that it is the right upper lobe. Furthermore, the pixels painted in gray are pixels (that is, observed voxels) shown in the gaze point information 603. In the gaze point information 603, the gaze points (x, y, z) (coordinates of voxels) at a time Ot are recorded in chronological order (in order of Ot=O1, O2, O3 . . . ). In this example of the tomographic image, observed are two voxels of "0 (outside the body surface)", fourteen voxels of "1 (right upper lobe)", nine voxels of "2 (right middle lobe)", ten voxels of "3 (right lower lobe)", six voxels of "4 (left upper lobe)", nineteen voxels of "5 (left lower lobe)", and twenty-three voxels of "9 (others)". By applying these voxels to the entire medical image data, it is possible to count the number of observed voxels for each label of the entire medical image data.

In the present embodiment, when Nok/Nak>0.8 is satisfied, where "Nok" is the number of observed voxels of the label k and "Nak" is the total number of voxels belonging to the label k, the anatomical structure denoted by the label k is determined as a gaze region (region of interest). Note that in the following description, observation is performed assuming that "right upper lobe" and "right lower lobe" are determined as regions of interest.

In step S305, the described region obtaining unit 110 obtains described regions, which are regions described in the report sentence, based on the region information obtained in step S301 and the report sentence obtained in step S303. In the present embodiment, described regions are obtained by performing keyword matching on the report sentence with anatomical structure names indicated by respective labels of the region information used as keywords. Note that matching may be performed by expanding the keyword using a synonym or ontology. For example, in the example of the report sentence shown in FIG. 5 (the example shown in the report sentence input region 502), "left upper lobe" and "right lower lobe" are obtained as the described regions.

In step S306, the determination unit 112 determines the consistency between the regions of interest obtained in step S303 and the described regions obtained in step S305. In the present embodiment, it is determined whether or not there is information that is included in the regions of interest but not in the described regions. That is, it is determined whether or not there is missing description, that is, there is a region that a medical doctor gazed at but is not included in the report sentence. In the above-described example, "right upper lobe" that is the region of interest is not included in the described region, and thus it is determined that there is missing description.

In step S307, the presenting information creation unit 114 creates presenting information based on the result determined in step S306. In the present embodiment, a message box is created as the presenting information. In the above-described example, since "right upper lobe" is not included in the described region, a message box notifying the fact is created. Then, in step S308, the presenting information creation unit 114 displays the created message box in the monitor 1005.

FIG. 7 shows an example of the presenting information displayed on the monitor 1005 according to the present embodiment. The presenting information is displayed in the form of a message box 704. Here, when the "YES" button in the message box 704 is pressed down, the report sentence can be corrected (re-input). That is, it is determined that a correction instruction is input in step S309, and the procedure returns to step S302 and it is possible to perform creation (editing) of the report sentence by the report creation unit 101. On the other hand, when the "NO" button is pressed down, the procedure advances to step S310, where the report creation unit 101 stores the report sentence in the magnetic disk 1003 or the like, and ends the report creation assistance processing.

Note that if, in step S306, the determination of consistency is successful (if it is determined that there is no missing description), for example, a message box indicating that fact may be created and displayed, and the user may be asked whether or not to continue creating the report sentence. Alternatively, if it is determined that there is no missing description, a configuration is also possible in which the report sentence is stored and the report creation ends, as with the above-described case where the "NO" button is pressed down.

As described above, according to the present embodiment, it is possible to call a medical doctor's attention to missing description with respect to a region that the medical doctor gazed at when having performed interpretation but is not described in the report sentence. Accordingly, it is possible for the medical doctor to create a report sentence without any missing description. Specifically, an advantageous effect can be expected in the interpretation style in which the medical doctor browses entire medical image data, and then describes report sentences altogether. Accordingly, the medical doctor can create an appropriate interpretation report.

Second Embodiment

The first embodiment has described a configuration in which "missing description" is detected based on determination of the consistency between a set of regions of interest and a set of described regions, and attention is called thereto. An interpretation report creation assistance apparatus according to a second embodiment calls a medical doctor's attention to a region that he or she described in the report sentences but did not gaze at when having performed interpretation. That is, the second embodiment describes a configuration for calling attention to a checking failure.

The configuration of the interpretation report creation assistance apparatus 100 according to the second embodiment is the same as that of the first embodiment (FIG. 1). Furthermore, the basic configuration of a computer that executes software thereby to realize interpretation report creation assistance processing of the assistance apparatus 100 is also the same as that of the first embodiment (FIG. 2). Furthermore, the flowchart illustrating the overall processing of the assistance apparatus 100 is the same as that of FIG. 3. However, the processing is partially different from the processing of the first embodiment. Hereinafter, the overall processing of the assistance apparatus 100 according to the second embodiment will be described with reference to the flowchart of FIG. 3.

The procedure from step S300 to step S305 and the procedure from step S307 to step S310 are the same as those of the first embodiment. In step S306, the determination unit 112 determines the consistency between the set of regions of interest obtained in step S304 and the set of described regions obtained in step S305.

In the present embodiment, it is determined whether or not there is information that is included in the described regions but not in the regions of interest. Note that, similarly to the first embodiment, a gaze region is used as a region of interest. That is, by determining whether or not there is a region that the medical doctor described but did not gaze at when having performed interpretation, it is determined whether or not there is a checking failure. For example, as in the example described in the first embodiment, a case is considered in which "right upper lobe" and "right lower lobe" are regions of interest and "left upper lobe" and "right lower lobe" are described regions. In this case, "left upper lobe" that is a described region is not included in the regions of interest, and thus it is determined that there is a checking failure.

Note that in the present embodiment, a message box including a schematic image is created as the presenting information that is presented in step S308. Specifically, a message box including an image that highlights an anatomical structure corresponding to the region of the checking failure is created. In the above-described example, "left upper lobe" is not included in the regions of interest, and thus a message box including a schematic image that highlights the "left upper lobe" is created. Then, the created message box is displayed on the monitor 1005.

FIG. 8 shows an example of the presenting information that is displayed on the monitor 1005 according to the present embodiment. The presenting information is displayed in the form of a message box 805. Here, when the "YES" button in the message box 805 is pressed down, it will be possible to perform interpretation again (that is, the procedure returns to the process of step S301). On the other hand, when the "NO" button is pressed down, the assistance apparatus 100 will store the report sentence and end the procedure.

Note that if it is determined in step S306 that there is no checking failure, the report sentence is stored and the procedure ends, as with the above-described case where "NO" button is pressed down. Note that a configuration is also possible in which if it is determined in step S306 that there is no checking failure, a message box indicating that fact is created and displayed, and a user is asked whether or not to continue creating the report sentence.

As described above, according to the second embodiment, it is possible to call a medical doctor's attention to a checking failure with respect to a region that he or she described in report sentences but did not gaze at when having performed interpretation. Accordingly, it is possible to prevent a region that a medical doctor did not gaze at from being described.

Furthermore, as another effect, the present embodiment can be expected to have an advantageous effect that, in the interpretation of a follow-up case in which a previous interpretation report is present, the previous interpretation report is used in creating a report sentence. That is, when a previous report is used and a description that is not suitable for the current state remains, a medical doctor is expected to be warned about a checking failure so as to realize the existence of an unnecessary description in a report on the current state. In the above-described configuration, it is possible for a medical doctor to create an appropriate interpretation report.

Modification 1

The first and second embodiments have described the examples in which in step S304, of regions of an axial tomographic image shown in the tomographic image display region 501, a gaze region for which gaze point information was obtained is used as a region of interest. However, the method for determining whether or not a region is a region of interest may not necessarily be a method for determining whether or not a gaze point was detected. In a modification 1, a displayed region of the axial tomographic image is handled as a region in which a gaze point was detected, and is determined as a region of interest. That is, the number of pixels of a part of the region A, described in the first embodiment, that is displayed on the monitor 1005 is used as the number NoA of pixels (voxels) in which a gaze point was detected of the region A.

FIGS. 9A and 9B are diagrams illustrating examples in which the regions displayed in the monitor are determined as regions of interest. FIG. 9A shows the example in which interpretation is performed in the state in which an axial tomographic image 906 is translated using an ordinary medical image viewer function. In this case, only a displayed part of the tomographic image display region 501 is determined as belonging to regions of interest. In this example, the hatched part of the axial tomographic image 906 is a displayed part of the medical image data at the time of interpretation. Accordingly, with respect to each medical region at least a part of which belongs to the hatched part of the medical image data (axial tomographic image 906), it is determined whether or not the medical region is a region of interest based on the ratio of the number of pixels displayed at the time of interpretation to the total number of pixels of this region. FIG. 9B shows the example in which interpretation is performed in the state in which the enlarged axial tomographic image 906 that is enlarged using the ordinary medical image viewer function is displayed. In this example, the hatched part of the axial tomographic image 906 is displayed regions at the time of interpretation. As described above, a region of the medically divided regions of the medical image data (axial tomographic image 906) at least a part of which belongs to the hatched part is a target for determination of whether or not it is a region of interest. Note that in the state in which the axial tomographic image 906 is reduced and displayed (that is, the entire axial tomographic image 906 is included in the tomographic image display region 501), the entire regions of the axial tomographic image 906 serve, of course, as regions of interest. Note that in the foregoing description, an anatomical structure region in which a ratio of a "part displayed at the time of interpretation" to the entire region exceeds a predetermined ratio is determined as a region of interest, but instead of the "part displayed at the time of interpretation", a "part of which display time at the time of interpretation is a predetermined time or more" may be determined as a region of interest. Alternatively, it is also possible to configure that the "predetermined ratio" for use in determining whether or not it is a region of interest is set to a lower value with an increase in the display time of the "part displayed at the time of interpretation".

Modification 2

In the first and second embodiments, regions of interest are obtained as a specific anatomical structure in step S304, described regions indicating an anatomical structure are obtained in step S305, and the consistency therebetween is determined in step S306. However, the method for determining the consistency is not limited to this method.

For example, in step S304, the region of interest obtaining unit 108 may obtain all of observed voxels (voxels in which a gaze point was present) as regions of interest, and converts the obtained voxels into groups of voxels for respective anatomical structures using the region information obtained in step S301. Then, in step S306, the determination unit 112 may determine the consistency based on how many voxels obtained as regions of interest are included in a group of voxels of each anatomical structure shown in the described region.

Modification 3

In the first and second embodiments, the determination of missing description and the determination of a checking failure are performed separately in the respective methods of the first embodiment and the second embodiment. However, the determination of missing description and the determination of a checking failure do not necessarily need to be performed separately, and may also be performed at the same time. That is, in the determination of the consistency, both missing description as described in the first embodiment and a checking failure as described in the second embodiment may be determined. Furthermore, in this case, a method for obtaining a set of regions of interest may be different between in the detection of missing description and in the detection of a checking failure. For example, a set of regions of interest for use in detecting missing description may be determined as a set of regions in which a gaze point has at least once been present, and a set of regions of interest for use in detecting a checking failure may be determined as a set of gaze regions.

Furthermore, although the first and second embodiments use display of the interpretation report creation screen and the presence of a gaze point to determine a region of interest, the present invention is not limited to this. For example, a configuration is also possible in which touch input means touch panel, or the like, is provided in the monitor 1005, and a position in which a user was interested during interpretation is touch-input. In this case, the region of interest obtaining unit 108 obtains a region of interest based on the touch input position.

As described above, according to the embodiments, it is possible to reduce occurrence of missing description or a checking failure at the time of creating an interpretation report.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-181591, filed Sep. 5, 2014, which is hereby incorporated by reference herein in its entirety.

The invention claimed is:

1. An assistance apparatus for assisting creation of an interpretation report, comprising:
 a memory storing a program; and
 one or more processors which, by executing the program, function as:
 a first obtaining unit obtaining a set of gaze regions, which are determined as regions that have been observed by a user during interpretation, of medical image data of a subject that is displayed as an interpretation target;
 a second obtaining unit obtaining a set of described regions, which are regions that correspond to a sentence of description of an interpretation report which is a result of the interpretation of the medical image data by the user;
 a determination unit determining consistency between the set of gaze regions and the set of described regions; and
 a display control unit controlling a monitor to display presentation information based on a result of the consistency determined by the determination unit, wherein
 the determination unit determines that there is a missing description in the interpretation report if there is a region that is included in the set of gaze regions but not in the set of described regions, and when the determination unit determines there is a missing description in the interpretation report, the display control unit controls the monitor to display an information of a region that is included in in the set of gaze regions but not included in the set of described regions,
 the determination unit determines that there is a checking failure with respect to the medical image data if there is a region that is included in the set of described regions but not in the set of gaze regions, and when the determination unit determines there is a checking failure with respect to the medical image data, the display control unit controls the monitor to display an information of a region that is included in the set of described regions but not included in the set of gaze regions, and
 the display control unit controls the monitor to display a message containing text indicating a region corresponding to a missing description when the determination unit determines that there is a missing description, and the display control unit controls the monitor to display a message including an image of an anatomical area emphasizing a region corresponding to a checking failure when the determination unit determines that there is a checking failure.

2. The apparatus according to claim 1, further comprising a gaze point tracking device, wherein
 the first obtaining unit determines a gaze region based on a gaze point of an interpreter tracked by the gaze point tracking device at a time of interpretation.

3. The apparatus according to claim 2, wherein the first obtaining unit obtains, from among medically divided regions of the medical image data, a region in which a ratio of a number of pixels in which a gaze point is detected to a total number of pixels included in the region exceeds a predetermined value, as the gaze region.

4. The apparatus according to claim 2, wherein the first obtaining unit obtains, from among medically divided regions of the medical image data, a region with respect to which a time during which a gaze point is detected in the region exceeds a predetermined time, as the gaze region.

5. The apparatus according to claim 1, wherein the first obtaining unit obtains, from among medically divided regions of the medical image data, a region at least a part of which is displayed on the monitor at a time of interpretation and in which a ratio of a number of displayed pixels to a total number of pixels included in the region exceeds a predetermined value, as a gaze region.

6. The apparatus according to claim 1, wherein the first obtaining unit determines a gaze region based on a display time at a time of interpretation of a displayed part of a medically divided region of the medical image data.

7. The apparatus according to claim 1, wherein the monitor includes a touch input unit, and
the first obtaining unit obtains the set of gaze regions based on a touch input position on the monitor that is displaying the medical image data.

8. The apparatus according to claim 1, wherein medically divided regions of the medical image data are regions obtained by division based on an anatomical structure, and
the second obtaining unit obtains, as the set of described regions, anatomical structure names described in the interpretation report.

9. The apparatus according to claim 8, wherein the second obtaining unit obtains the set of described regions from the interpretation report by keyword matching in which anatomical structure names of all regions obtained by dividing the medical image data based on the anatomical structure are used as keywords.

10. A method for controlling an assistance apparatus for assisting creation of an interpretation report, comprising:
obtaining a set of gaze regions, which are determined as regions that have been observed by a user during interpretation, of medical image data of a subject that is displayed as an interpretation target;
obtaining a set of described regions, which are regions that correspond to a sentence of description of an interpretation report which is a result of the interpretation of the medical image data by the user;
determining consistency between the set of gaze regions and the set of described regions; and
controlling a monitor to display presentation information based on a result of the determined consistency, wherein
the step of determining consistency comprises determining there is a missing description in the interpretation report if there is a region that is included in the set of gaze regions but not in the set of described regions, and determining there is a checking failure with respect to the medical image data if there is a region that is included in the set of described regions but not in the set of gaze regions,
the step of controlling comprises controlling the monitor to display an information of the region that is included in the set of gaze regions but not included in the set of described regions when it is determined that there is the missing description, and controlling the monitor to display an information of the region that is included in the set of described regions but not included in the set of gaze regions when it is determined that there is the checking failure, and
the step of controlling further comprises controlling the monitor to display a message containing text indicating a region corresponding to a missing description when it is determined that there is a missing description, and controlling the monitor to display a message including an image of an anatomical area emphasizing a region corresponding to a checking failure when it is determined that there is a checking failure.

11. A non-transitory computer-readable storage medium storing a program for causing a computer to execute a method for controlling an assistance apparatus for assisting creation of an interpretation report, comprising:
obtaining a set of gaze regions, which are determined as regions that have been observed by a user during interpretation, of medical image data of a subject that is displayed as an interpretation target;
obtaining a set of described regions, which are regions that correspond to a sentence of description of an interpretation report which is a result of the interpretation of the medical image data by the user;
determining consistency between the set of gaze regions and the set of described regions; and
controlling a monitor to display presentation information based on a result of the determined consistency, wherein
the step of determining consistency comprises determining there is a missing description in the interpretation report if there is a region that is included in the set of gaze regions but not in the set of described regions, and determining there is a checking failure with respect to the medical image data if there is a region that is included in the set of described regions but not in the set of gaze regions,
the step of controlling comprises controlling the monitor to display an information of the region that is included in the set of gaze regions but not included in the set of described regions when it is determined that there is the missing description, and controlling the monitor to display an information of the region that is included in the set of described regions but not included in the set of gaze regions when it is determined that there is the checking failure, and
the step of controlling further comprises controlling the monitor to display a message containing text indicating a region corresponding to a missing description when it is determined that there is a missing description, and controlling the monitor to display a message including an image of an anatomical area emphasizing a region corresponding to a checking failure when it is determined that there is a checking failure.

12. An apparatus for assisting medical diagnosis, the apparatus comprising:
at least one processor; and
a memory storing a program including instructions executed by the at least one processor to perform a process including:
obtaining a set of gaze regions, which are determined as regions that have been observed by a user during interpretation, of medical image data of a subject that is displayed as an interpretation target;
obtaining a set of described regions, which are regions that correspond to a sentence of description of an interpretation report which is a result of the interpretation of the medical image data by the user;

determining consistency between the set of gaze regions and the set of described regions; and controlling a monitor to display presentation information based on a result of the determined consistency, wherein the consistency determination comprises determining that there is a missing description in the interpretation report if there is a region that is included in the set of gaze regions but not in the set of described regions, and determining there is a checking failure with respect to the medical image data if there is a region that is included in the set of described regions but not in the set of gaze regions, the controlling comprises controlling the monitor to display an information of the region that is included in the set of gaze regions but not included in the set of described regions when it is determined that there is the missing description, and controlling the monitor to display an information of the region that is included in the set of described regions but not included in the set of gaze regions when it is determined that there is the checking failure, and the controlling further comprises controlling the monitor to display a message containing text indicating a region corresponding to a missing description when the consistency determination determines that there is a missing description, and controlling the monitor to display a message including an image of an anatomical area emphasizing a region corresponding to a checking failure when the consistency determination determines that there is a checking failure.

* * * * *